United States Patent [19]

Blank et al.

[11] Patent Number: 5,072,053

[45] Date of Patent: Dec. 10, 1991

[54] 1,3-DI-ARYLMETHOXY-4,6-DINITRO-BENZENES, PROCESS FOR THEIR PREPARATION AND PROCESS FOR THE PREPARATION OF 4,6-DIAMINORESORCINOL

[75] Inventors: Heinz U. Blank, Odenthal; Uwe Heinz, Cologne, both of Fed. Rep. of Germany

[73] Assignee: Bayer Aktiengesellschaft, Leverkusen, Fed. Rep. of Germany

[21] Appl. No.: 526,357

[22] Filed: May 21, 1990

[30] Foreign Application Priority Data

Jun. 10, 1989 [DE] Fed. Rep. of Germany ....... 3919045

[51] Int. Cl.$^5$ ..................... C07C 43/20; C07C 205/35
[52] U.S. Cl. .................................... 568/586; 568/932; 568/939
[58] Field of Search .................. 568/586, 939, 932

[56] References Cited

U.S. PATENT DOCUMENTS

| | | | |
|---|---|---|---|
| 4,168,388 | 9/1979 | Lavagnino et al. | 568/586 X |
| 4,537,999 | 8/1985 | Ogawa et al. | 568/586 X |
| 4,686,301 | 8/1987 | Papenfuhs et al. | 568/586 X |
| 4,695,656 | 9/1987 | Reh et al. | 568/586 X |
| 4,868,347 | 9/1989 | Blank et al. | 568/937 |

Primary Examiner—Robert L. Stoll
Assistant Examiner—Chhaya Sayala
Attorney, Agent, or Firm—Sprung Horn Kramer & Woods

[57] ABSTRACT

The new 1,3-di-arylmethoxy-4,6-dinitrobenzenes of the formula

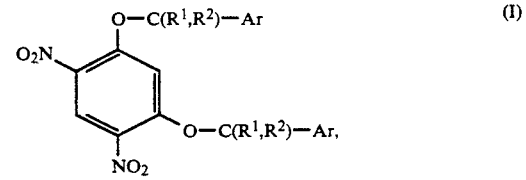

in which
$R^1$ and $R^2$ independently of one another denote hydrogen or $C_1$–$C_4$-alkyl and
Ar represents $C_6$–$C_{12}$-aryl, can be prepared by reaction of 1,3-dihalogeno-4,6-dinitro-benzenes of the formula

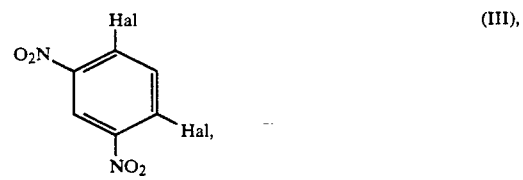

in which Hal represents chlorine or bromine, with an arylmethanol of the formula

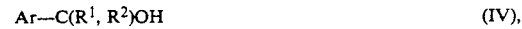

in which $R^1$, $R^2$ and Ar have the said meaning, and a strong base in the temperature range from 0° to 100° C.

These di-arylmethoxy-dinitro-benzenes can be converted into 4,6-diaminoresorcinol by catalytic reduction with hydrogen.

3 Claims, No Drawings

1,3-DI-ARYLMETHOXY-4,6-DINITRO-BENZENES, PROCESS FOR THEIR PREPARATION AND PROCESS FOR THE PREPARATION OF 4,6-DIAMINORESORCINOL

BACKGROUND OF THE INVENTION

1. Field of the Invention

The present invention relates to new di-arylmethoxy-dinitro-benzenes, a process for their preparation from dihalogeno-dinitro-benzenes and arylmethanols, as well as their further conversion to 4,6-diaminoresorcinol by catalytic hydrogenation.

Diaminoresorcinol is used as a monomer unit in the synthesis of polybenzoxazoles, which, for example, are used as starting material for electroactive polymers (DE-OS 3,341,627).

2. Description of the Related Art

At present diaminoresorcinol is prepared by nitration of diacetylresorcinol, removal of the protective groups and reduction of the nitro groups on a Pd/activated charcoal catalyst (Macromolecules 14 (1981), 909). The critical step in this process is the nitration. In nitric acid is proceeds ony with approximately 30% yield. Since, the process must also be carried out at high dilution, the space yield is only about 10 g/l or 0.05 mole/l. The removal of the protective group in a further process step is carried out with similarly unfavourable space yield. Styphnic acid (2,4,6-trinitroresorcinol) is formed as by-product, which leads to deflagrations at elevated temperatures (Bielstein, Main Work volume 6, p. 830) and therefore constitutes a safety problem. Since, on the one hand, the reaction is strongly exothermic and, on the other hand, exothermic decomposition reactions occur at a temperature which is only slightly above room temperature, a safe reaction procedure is difficult.

According to U.S. Pat. No. 4,745,232, the formation of dinitroresorcinol from diacetylresorcinol is said to proceed without the undesired formation of styphnic acid and with a 65% yield if the process is carried out using "white" nitric acid (presumably $HNO_3$ which is free from $NO_2$ is intended here) and with addition of urea as a reagent for the control of the nitrosyl ions, or if the process is carried out with nitric acid in sulphuric acid. With these procedures the space yield improves to 65 g/l (0.35 mole/l) and to 40 g/l (0.2 mole/l) respectively but, for this improvement the increased expense mentioned is necessary.

Because of the difficulties mentioned it has been tried to obtain diaminoresorcinol from another starting material. Thus, in EP 266,222 it is proposed to nitrate 1,2,3-trichlorobenzene in a sulphuric acid/nitric acid mixture to 1,2,3-trichloro-4,6-dinitro-benzene and to convert this compound, using an alkali metal hydroxide in methanol/water, into 1,3-dihydroxy-2-chloro-4,6-dinitrobenzene. The reduction of the latter compound on a Pd/activated charcoal catalyst gives diaminoresorcinol. However this process has the disadvantage that the dihydroxy compound of the second process step must be extracted with ethyl acetate, as a consequence of which the space yield drops to about 75 g/l (0.32 mole/l); after the said extraction the dihydroxy compound is isolated by evaporation of the ethyl acetate phase.

SUMMARY OF THE INVENTION

The present invention relates to 1,3-di-arylmethoxy-4,6-dinitro-benzenes of the formula

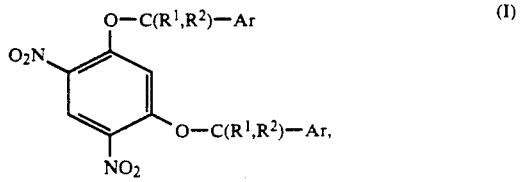

in which
$R^1$ and $R^2$ independently of one another denote hydrogen or $C_1$-$C_4$-alkyl and
Ar represents $C_6$-$C_{12}$-aryl.

The invention additionally relates to a process for the preparation of 1,3-di-arylmethoxy-4,6-dinitrobenzoles of the formula (I), which is characterized in that 1,3-dihalogeno-4,6-dinitro-benzenes of the formula

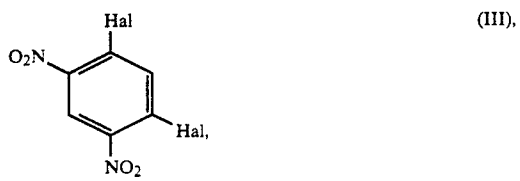

in which Hal represents chlorine or bromine, are reacted with 2 to 5 moles of an arylmethanol of the formula

in which $R^1$, $R^2$ and Ar have the said meaning, and 2 to 5 equivalents of a strong base in the temperature range of from 0° to 100° C. in the presence of an inert solvent.

The invention additionally refers to a process for the preparation of 4,6-diaminoresorcinol, which is characterized in that a) a 1,3-dihalogeno-4,6-dinitro-benzene of the formula (III) is reacted in the liquid phase with 2 to 5 moles of an arylmethanol of the formula (IV), Hal, $R^1$, $R^2$ and Ar having the said range of meaning, and 2 to 5 equivalents of a strong base in the temperature range from 0° to 100° C. and b) the 1,3-di-arylmethoxy-4,6-dinitro-benzene of the formula (I) obtained in accordance with a) is hydrogenated in heterogeneous phase using a platinum metal supported catalyst in an amount of 0.1 to 10% by weight of the platinum metal, relative to the weight of the 1,3-di-arylmethoxy-4,6-dinitrobenzene, at 1 to 30 bar $H_2$ pressure and in the temperature range from 20° to 100° C.

DETAILED DESCRIPTION OF THE INVENTION $R^1$ and $R^2$ independently of one another denote hydrogen or $C_1$-$C_4$-alkyl, such as methyl, ethyl, propyl, isopropyl, butyl, isobutyl or tert.-butyl, preferentially hydrogen or methyl and particularly preferentially hydrogen.

Ar represents $C_6$-$C_{12}$-aryl, such as phenyl, naphthyl or biphenylyl, preferably phenyl.

Hal represents chlorine or bromine, preferably chlorine.

The invention relates preferentially to 1,3-di-phenylmethoxy-4,6-dinitro-benzenes of the formula

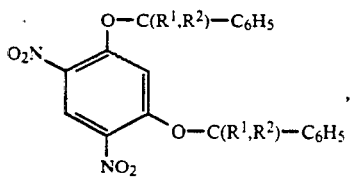

(II)

in which $R^1$ and $R^2$ independently of one another denote hydrogen or $C_1$-$C_4$-alkyl.

The invention particularly preferentially relates to 1,3-dibenzyloxy-4,6-dinitro-benzene.

The preparation process for the substances of the formula (I) uses 1,3-dihalogeno-4,6-dinitro-benzenes of the formula (III), which can be prepared by nitration of m-dichlorobenzene or m-dibromobenzene, as starting materials. These starting materials are obtainable in a yield of 70% and a space yield of 0.47 mole/l. In this nitration a higher temperature than in the case of the nitration of diacetylresorcinol is also permissible, without the occurrence of undesired decomposition reactions (DE-OS 3,408,301).

The starting material (III) is reacted with 2 to 5 moles, preferably with 2 to 3 moles, of an arylmethanol of the formula (IV) and with 2 to 5 equivalents, preferably with 2 to 3 equivalents, of a strong base. The strong base used is one or more from the group comprising the alkali metals, such as lithium, sodium, potassium, rubidium or caesium, preferably sodium or potassium, the alkaline earth metals, such as magnesium, calcium, strontium or barium, preferably magnesium or calcium, the alkali metal hydroxides, such as lithium hydroxide, sodium hydroxide, potassium hydroxide, rubidium hydroxide or caesium hydroxide, preferably sodium hydroxide or potassium hydroxide, the alkaline earth metal hydroxides, such as magnesium hydroxide, calcium hydroxide, strontium hydroxide or barium hydroxide, preferably magnesium hydroxide or calcium hydroxide, the alkali metal carbonates, such as lithium carbonate, sodium carbonate, potassium carbonate, rubidium carbonate or caesium carbonate, preferably sodium carbonate or potassium carbonate, and the alkaline earth metal carbonates, such as magnesium carbonate, calcium carbonate, strontium carbonate or barium carbonate, preferably magnesium carbonate or calcium carbonate. Preferentially a strong base from the group comprising the alkali metals, the alkali metal hydroxides and alkali metal carbonates, particularly preferentially from the group sodium metal, sodium hydroxide and sodium carbonate is used. The arylmethanols can likewise also be used directly in the form of their alcoholates.

The reaction is carried out in the temperature range from 0° to 100° C., preferably in the range from 40° to 70° C.

A suitable inert solvent is an aliphatic, aromatic or alkylaromatic hydrocarbon, a halogenated aromatic hydrocarbon or additional arylmethanol of the formula (IV) in excess of the said 2 to 5 moles, provided such an arylmethanol is liquid at the desired reaction temperature. Examples of such solvents are: pentane, hexane, heptane, octane, decane, dodecane and higher molecular weight, straight-chain or branched aliphatic hydrocarbons, as well as mixtures thereof, such as ligroin or petroleum ether, benzene, toluene, ethylbenzene, chlorobenzene, bromobenzene, dichlorobenzene, dibromobenzene, chlorotoluene, dichlorotoluene or cyclohexane. Of course mixtures of several of the said solvents can also be used.

Examples of arylmethanols, which can be used in excess above the said 2 to 5 equivalents and thus at the same time serve as reactant and inert solvent, are benzyl alcohol and α-phenylethanol. Preferentially, in this context, such a use in the case of benzyl alcohol may be mentioned. In this case an arylmethanol of this type, preferably the benzyl alcohol, is used in an amount of 3 to 20 parts by weight, preferably 3 to 10 parts by weight, relative to 1 part by weight of the dihalogeno-dinitro-benzene.

The reaction is not dependent upon the pressure above the reaction mixture and for the sake of simplicity is therefore carried out at atmospheric pressure. An increased pressure could be useful if a low-boiling solvent is to be kept in the liquid phase; in this case it is preferable to carry out the process under the autogenious pressure developed by the system.

The reaction, according to the invention, of the dihalogeno-dinitro-benzenes (III) with the arylmethanols (IV) in the presence of the said base proceeds quickly (laboratory batches generally within 30 min.) and produces high yields, which as a rule exceed 90%. In many cases the reaction product is insoluble in the reaction medium and can therefore be isolated by simple filtration. The inorganic by-products can then be removed with water, for which purpose the reaction product (I) is made into a slurry with water and again filtered with suction. However it is also possible to wash the reaction product originally filtered off with water on the suction filter. With larger batches centrifuging or other measures known to the person skilled in the art can, of course, be used instead of filtration. The space yield that can be achieved is about 0.75 mole/l and is therefore considerably higher than in the processes known hitherto.

The di-arylmethoxy-dinitro-benzenes (I) can be converted into diaminoresorcinol by catalytic hydrogenation. In this reaction a simultaneous hydrogenation of the nitro groups to the amino groups and a splitting off of the arylmethoxy groups takes place. The catalysts used are platinum metals, such as palladium, platinum, rhodium or ruthenium, preferably palladium or platinum, on a suitable carrier. Suitable carriers, such as activated charcoal, $SiO_2$, $Al_2O_3$, pumice and others, are known to the person skilled in the art. The platinum metal supported catalyst is used in an amount of 0.1 to 10% by weight of the platinum metal, preferably 0.2 to 2% by weight, relative to the weight of (I). The hydrogenation is carried out at a $H_2$ pressure of 1 to 30 bar and in the temperature range from 20° to 100° C., preferably in the range from 20° to 50° C.

An alcohol, an ether, an aromatic or alkylaromatic hydrocarbon, an organic acid or a mixture of several of these can be used as the liquid reaction medium for the hydrogenation. Examples of such liquid reaction media are: methanol, ethanol, propanol, isopropanol, butanol, isobutanol, tetrahydrofuran, dioxane, benzene, toluene, xylene, dimethoxy-ethane, diethoxyethane, 1,2-dimethoxy-propane and other glycol mono- and di-ethers, acetic acid, propionic acid or mixtures of these. Methanol, ethanol, propanol, butanol, tetrahydrofuran, dioxane, dimethoxy-ethane, diethoxy-ethane, 1,2-dimethoxy-propane and other glycol mono- and di-ethers, acetic acid, propionic acid, toluene or a mixture of several of these are preferentially suitable as liquid reaction media for the hydrogenation. In the case of water-soluble liquid reaction media, the organic portion of this reaction medium can be replaced to the extent of up to 75% by weight by water or dilute aqueous mineral acid. The total liquid reaction medium for the hydrogenation is used in an amount of 5 to 25 parts by weight, preferably 7 to 15 parts by weight, relative to 1 part by weight of (1).

It is known that in catalytic hydrogenations of nitro compounds to the associated amines care must be taken to ensure sufficient solubility of the starting materials in the reaction medium; it is also known that the amines formed, like amines in general, inhibit platinum metal catalysts in the course of the reaction, so that an addition of acid to bind the amines formed is advantageous (Houben-Weyl, Handbuch der organischen Chemie (Handbook of Organic Chemistry), volume 4/1c, p. 509 (1980)). In the present case it is therefore surprising that the catalytic hydrogenation, for example, in a reaction medium of tetrahydrofuran and an aqueous mineral acid, proceeds with high yields, even though the nitro compound is almost insoluble in this reaction medium. It is also surprising that the reduction in an alcohol also proceeds without the addition of acid, even though the product formed is even a diamino compound.

EXAMPLE 1

1,3-Dibenzyloxy-4,6-dinitro-benzene, NaOH as base 9.60 g (0.24 mole) of sodium hydroxide were added to 130 ml of benzyl alcohol, with stirring. After all of the sodium hydroxide had dissolved, 23.7 g (0.1 mole) of 1,3-dichloro-4,6-dinitro-benzene were added. An exothermic reaction then occurred. The educt was added at such a rate that a temperature of 50° C. was not exceeded. On completion of the addition, the mixture was stirred for a further 30 min. at 50° C. The mixture was cooled to room temperature and filtered with suction. To remove inorganic salts, the material on the suction filter was made into a slurry with 500 ml of water and again filtered with suction and dried. 34.23 g (0.09 mole=88.9%) of product were obtained. According to thin-layer chromatography (eluant 50 parts of xylene, 20 parts of ethyl acetate, 10 parts of acetic acid) the substance is a single compound.

| | Elementary analysis: | |
|---|---|---|
| | calculated | found |
| C | 63.4% | 62.9% |
| H | 4.2% | 4.4% |
| N | 7.4% | 7.4% |

IR, ¹H-NMR and mass spectra are in agreement with the structure.

EXAMPLE 2

1,3-Dibenzyloxy-4,6-dinitro-benzene, sodium as base 11 g (0.48 mole) of sodium were dissolved in 400 ml of benzyl alcohol. The solution was then cooled to room temperature and the 1,3-dichloro-4,6-dinitro-benzene (49.3 g=0.208 mole) added at such a rate that the temperature did not exceed 55° C. During this addition the mixture was cooled in an ice bath. It was stirred for a further 15 min. at 50° C. and then cooled to 50° C. and the product was filtered off with suction. The material on the suction filter was made into a slurry with 1 l of water, stirred for 1 hour and again filtered off with suction. After washing with water and drying, 70.4 g (0.19 mole=91.4%) of product remained.

EXAMPLE 3

4,6-Diaminoresorcinol dihydrochloride, methanol as solvent 57 g (0.15 mole) of 1,3-dibenzyloxy-4,6-dinitrobenzene were added to 700 ml of methanol. 5 g of Pd/C (5%) were added to the mixture. The mixture was hydrogenated at 75° C. and 3,5 bars hydrogen pressure until no further hydrogen was taken up. 500 ml of hydrochloric acid (about 37%) were added to the batch and the resulting mixture was filtered with suction. The material on the suction filter was washed 5 times, in each case with 100 ml of water. 500 ml of hydrochloric acid (about 37%) were again added to the combined water-washings and the mixture stirred for 1 hour. The precipitate was filtered off with suction, washed 4 times with 100 ml of acetone to displace the water and dried in a desiccator. 26.34 g (0.124 mole=82.4%) of product were obtained. All operations were carried out under nitrogen.

| | Elementary analysis | |
|---|---|---|
| | calculated | found |
| C | 33.8% | 33.5% |
| H | 4.7% | 4.5% |
| N | 13.1% | 12.9% |
| Cl | 33.3% | 32.9% |

EXAMPLE 4

4,6-Diaminoresorcinol dihydrochloride, tetrahydrofuran/ hydrochloric acid as solvent.

57 g (0.15 mole) of 1,3-dibenzyloxy-4,6-dinitrobenzene were added to 500 ml of hydrochloric acid (about 37%) and 200 ml of tetrahydrofuran. 20 g of Pd/C (5%) were added to the mixture. The mixture was hydrogenated at 75° C. and 3.5 bars hydrogen pressure until no further hydrogen was taken up. The batch was filtered with suction. The material on the suction filter was washed 3 times, each time with 250 ml of water. 1,000 ml of hydrochloric acid (about 37%) were again added to the combined water-washings and the mixture was stirred for 1 hour. The precipitate was filtered off with suction, washed 4 times with 100 ml of acetone to displace the water and dried in a desiccator. 25.00 g (0.117 mole=78.2%) of product were obtained. All operations were carried out under nitrogen.

EXAMPLES 5-10 reduction

Examples 5 to 10 were carried out in the same way as Example 3. The solvent and the quantities used and the yields are summarized in Table 1.

TABLE 1

| Ex. | Quantity (g) of 1,3-dibenzyloxy-4,6-dinitro-benzene used | Solvent Type | Solvent Amount ml | Catalyst 5% Pd/C g | Temperature °C. | H₂ pressure bar | Yield g | Yield % of theory |
| --- | --- | --- | --- | --- | --- | --- | --- | --- |
| 5 | 50 | Methanol | 300 | 2.1 | 50 | 3.5 | 26.2 | 93.7 |
| 6 | 24.5 | Methanol | 300 | 0.5 | 50 | 3.5 | 12.2 | 89 |
| 7 | 24.5 | 1-Butanol | 300 | 2.1 | 50 | 3.5 | 11.7 | 84.9 |
| 8 | 24.5 | 1,2-Dimethoxyethane | 300 | 2.1 | 50 | 3.5 | 11.7 | 85.5 |
| 9 | 24.5 | Acetic acid/water = 4/1 | 300 | 2.1 | 50 | 3.5 | 10.8 | 78.5 |
| 10 | 24.5 | Toluene | 300 | 2.1 | 50 | 3.5 | 11.2 | 81.4 |

What is claimed is:

1. A 1,3-di-arylmethoxy-4,6-dinitrobenzene of the formula

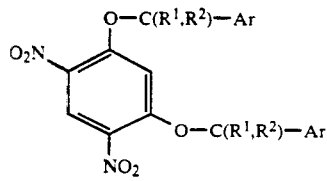

in which
R¹ and R² independently of one another denote hydrogen or $C_1$-$C_4$-alkyl and
Ar represents $C_6$-$C_{12}$-aryl.

2. A 1,3-Di-phenylmethoxy-4,6-dinitro-benzene of the formula

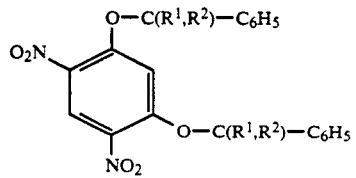

in which R¹ and R² independently of one anothe denote hydrogen or $C_1$-$C_4$-alkyl.

3. 1,3-Dibenzyloxy-4,6-dinitro-benzene.

* * * * *